United States Patent [19]
Mori et al.

[11] Patent Number: 5,898,176
[45] Date of Patent: Apr. 27, 1999

[54] ELEMENT ANALYZING METHOD WITH A SCANNING TYPE PROBE MICROSCOPE AND SUPER SHORT HIGH VOLTAGE PULSE APPLYING METHOD USING THE ELEMENT ANALYZING METHOD

[75] Inventors: Yuzo Mori, Katano; Masao Sakamoto, Osaka, both of Japan

[73] Assignee: Japan Science and Technology Corp., Kawaguchi, Japan

[21] Appl. No.: 08/849,719

[22] PCT Filed: Dec. 26, 1995

[86] PCT No.: PCT/JP95/02702

§ 371 Date: Sep. 16, 1997

§ 102(e) Date: Sep. 16, 1997

[87] PCT Pub. No.: WO96/20406

PCT Pub. Date: Jul. 4, 1996

[30] Foreign Application Priority Data

Dec. 27, 1994 [JP] Japan .............................. H06-325661
Dec. 27, 1994 [JP] Japan .............................. H 06-325662

[51] Int. Cl.⁶ .................................................. H01J 37/28
[52] U.S. Cl. ............................................................ 250/307
[58] Field of Search .................................. 250/307, 306; 73/105

[56] References Cited

U.S. PATENT DOCUMENTS 5,661,301  8/1997  Weiss ...................................... 250/307

Primary Examiner—Kiet T. Nguyen
Attorney, Agent, or Firm—Armstrong, Westerman, Hattori, McLeland & Naughton

[57] ABSTRACT

A high space resolving power of the scanning type probe microscope combined with an element analysis and the chemical bond condition analyzing ability of an Auger electronic spectroscopic method, and the energy analyzing results of the Auger electron generated by the high energy electron projection are considered, whereby it is possible to determine the three dimensional coordinate of the atomic nucleus of one atom of the surface, analyze the element thereof and analyze the chemical bond condition. While during the inherent operation of the scanning type probe microscope which may observe the atomic order image or in stopping the operation thereof, a super short AC or DC high voltage pulse is once or repeatedly applied between the probe and the sample, so that valent electron spherically symmetrically distributed about a nucleus or an internal shell electron of the sample is excited, and an energy analysis and a counter analysis of a photon or an Auger electron discharged in accordance with the excitation is performed. A determination of a three-dimensional coordinates of a nucleus for every one atom of the surface of the sample, the element analysis thereof, and a measurement of a surface distribution concerning a chemical bond condition analysis are carried out to obtain an atomic image of the surface of the sample including element and chemical bond information.

20 Claims, 8 Drawing Sheets

ELEMENT ANALYZING METHOD WITH A SCANNING TYPE PROBE MICROSCOPE AND SUPER SHORT HIGH VOLTAGE PULSE APPLYING METHOD USING THE ELEMENT ANALYZING METHOD

BACKGROUND OF THE INVENTION

1. Field of the Invention

The present invention is made for further developing the application range of a scanning type probe microscope through which a sample surface may be observed substantially in an element order by utilizing a tunnel effect between a probe and a sample. The present invention relates to an element analyzing method with a scanning type probe microscope which may determine a three-dimensional atomic nucleus coordinates for every one surface atom, analyze the element and analyze a condition of chemical bonds, which will become important in a semiconductor industry, a biotechnology industry and the like. The present invention also relates to a super short pulse high voltage applying method in a scanning probe microscope that may repeatedly apply a super short pulse high voltage between a probe and a sample for realizing the above-described element analyzing method.

For example, according to the present invention, it is possible to inspect and specify the surface element distribution and the impurity element distribution in the atomic order in a silicon wafer, gallium arsenic wafer and a ULSI. The invention contributes to the development of the semiconductor industry. Also, the invention contributes to realizing atom craft by the atom maneuver, is available for the surface atomic structure analysis for contributing realization and discovering a mechanism of a high temperature super conductor, and is useful for the determination of the atomic nucleus array of DNA or the like in the life science, the element analysis and the chemical bond condition analysis, leads to a way to the replacement of DNA such as composition of new DNA, severing and combining DNA and contributes to the development of the biotechnology industry.

2. Description of the Related Art

The method which may perform the most minute area/polarity surface layer analysis among the conventional element analysis and chemical bond condition analyzing technology is a scanning type Auger electron spectroscopic analysis. Even by the up-to-date technique, the measurement range is several tens of nm in diameter and several nm in depth. It is impossible to measure the surface atom one by one.

On the other hand, with the scanning type probe microscope (SPM) such as a scanning type tunnel microscope (STM) and an atomic interactive force microscope (AFM), it is possible to perform the real space resolving power in the atomic order. It is however not always easy to perform the interpretation of the measurement result. In the scanning type tunnel microscope, a bias voltage is applied between the probe and the sample arranged at an interval of about 10 Å. While keeping the tunnel current flowing through the probe and the sample by controlling the interval between the probe and the sample (in Z direction), the probe scans along the concave and convex of the sample surface (XY surface), so that an atomic image of the sample surface may be depicted from the control voltage of the piezoelectric element in the Z direction. Also, in the scanning type atomic interactive force microscope, the interval between the probe provided at a "lever" having a small spring constant and the sample is shortened to such an extent that the interatomic force (repulsive force) is applied between the two components (2 to 3 Å). The probe scans along the convex and concave of the sample surface. As a result, the "lever" is deformed in response to the convex and concave of the sample surface. It is therefore possible to depict the atomic image of the sample surface by measuring the deformation of the atomic order by the STM, a laser beam reflective measuring method or a light interference measuring method.

However, the above-described bias voltage applied between the probe and the sample is limited to a low voltage DC or a low voltage low frequency AC of several Vs, and there is no case where the super short pulse high voltage is applied. Even the conventional scanning type probe microscope having the real space resolving power in the atomic order mainly measures the electron condition or the like of valence electron. The meaning of observing the electron image is not the observation of the position (coordinate) of the atomic nucleus.

SUMMARY OF THE INVENTION

In view of the foregoing status of the prior art, a first object of the present invention is to determine the three dimensional coordinate of the atomic nucleus of one atom of the surface, analyze the element thereof and analyze the chemical bond condition which have been impossible in the state of the art.

More specifically, according to the invention, the high space resolving power of the scanning type probe microscope is combined with the element analysis and the chemical bond condition analyzing ability of the Auger electronic spectroscopic method whereby it is possible to determine the three dimensional coordinate of the atomic nucleus of one atom of the surface, analyze the element thereof and analyze the chemical bond condition. Also, in case of the combination with the energy analysis of the photon generated by the projection of the high energy, it is possible to provide the analyzing method with the scanning type probe microscope that may determine the three dimensional coordinate of the atomic nucleus of one atom of the surface, analyze the element thereof and analyze the chemical bond condition.

Also, in order to realize the element analyzing method with the above-described scanning probe microscope, it is possible to repeatedly apply the super short pulse high voltage between the scanning type probe microscope and the sample without deforming the waveform and with high efficiency. For this reason, a second object of the present invention is to provide the super short pulse high voltage applying method in the scanning type probe microscope. Namely, the super short pulse high voltage is repeatedly applied to the probe or the sample to thereby excite the internal shell electron of the sample or the probe by the high energy electron projected from the probe or the sample (spherical symmetrically distributed valence electrons about the nucleus in some cases). When the electron having a higher energy level than that of the internal shell electron is dropped into the void produced by the excitation, the photon or Auger electron is emitted. Accordingly, the energy analysis and counter analysis are carried out for the photon or the Auger electron; that is, the information of the internal shell electrons or the like spherically symmetrically distributed about the nucleus is analyzed for every one atom. It is thus possible to readily determine the three dimensional coordinate of the atomic nucleus of one atom of the surface, analyze the element and analyze the chemical bond condition, which could not be attained by the conventional scanning type probe microscope.

Namely, an object of the present invention is to realize a novel scanning type probe microscope which may obtain the information of the nucleus that could not be measured by the conventional scanning type probe microscope.

First of all, the scanning type probe microscope according to the present invention means a microscope which has a real space resolving power of substantially atomic order generated by a scanning type tunnel, microscope such as a so-called scanning tunnel microscope, an interatomic force microscope and a scanning type close-up optical microscope.

In the element analyzing method with the scanning type probe microscope according to the present invention, an AC or DC super short pulse high voltage is applied between the probe and the sample so that the high space resolving power of the scanning type probe microscope and the element analysis and the chemical bond condition analysis of the Auger electron spectroscopic method are combined with each other. It is therefore possible to determine the three dimensional coordinate of the atomic nucleus of one atom of the surface, analyze the element and analyze the chemical bond condition. Also, in combination with the energy analysis of the photon generated by the high energy electron projection, it is possible to determine the three dimensional coordinate of the atomic nucleus of one atom of the surface, analyze the element thereof and analyze the chemical bond condition.

Namely, according to the present invention, there is provided an element analyzing method with a scanning type probe microscope, characterized in that, a distance between an end of a probe and a sample is extremely shortened; while during the inherent operation of the scanning type probe microscope or in stopping the operation thereof, a super short pulse high voltage of AC or DC such that a photon or an Auger electron is discharged from the sample and an atom of an end of the probe is once or repeatedly applied between the probe and the sample, or after the super short pulse high voltage has been applied, the probe and the sample are moved relative to each other to scan the surface of the sample with the probe to obtain an atomic order image of the surface of the sample; an energy and the number of photons and the number of electrons of the photons and the Auger electrons discharged to the outside of the surface from the sample and the probe atom are analyzed to thereby perform the element analysis and a chemical bond condition analysis of the probe atom; and a determination of a three-dimensional coordinate of a nucleus for every one atom of the surface of the sample, the element analysis thereof, and a measurement of a surface distribution concerning a chemical bond condition analysis are carried out to obtain an atomic image of the surface of the sample including element and chemical bond information.

In such an element analyzing method with the scanning type probe microscope according to the present invention, while during the inherent operation of the scanning type probe microscope or in stopping the operation thereof, a super short pulse high voltage of AC or DC is once or repeatedly applied between the probe and the sample, or after the super short pulse high voltage has been applied, the probe and the sample are moved relatively to each other to scan the surface of the sample. At this time, when the internal shell electron (which may be a valence electron in some cases) of the facing atom is excited by a high energy electron beam emitted from one atom (ideally) of the probe or ideally one atom on the surface of the sample, the energy and the number of the Auger electron and the number of the photon emitted only in a direction substantially perpendicular to the high energy electron beam are analyzed to thereby make it possible to determine the three dimensional coordinate of the atomic nucleus of one atom of the surface, analyze the element thereof and analyze the chemical bond condition.

In more detail, the probe end of the scanning type probe microscope and the surface of the sample are located very close to each other to reduce the distance therebetween, during the inherent operation or the stopping of the operation under the condition that the atomic order image may be observed through the conventional scanning type probe microscope, while the AC or DC super short pulse high voltage is once or repeatedly applied between the surface of the sample and the probe, or after the application, the probe and the surface of the sample are moved relative to each other. The above-described inherent operation as the scanning type probe microscope is re-started for scanning. In this case, the high energy electron emitted from the probe (or the surface of the sample) excites the internal shell electron (which may be a valence electron in some cases) in the orbital, for example, designated by A. Then, an electron along another orbital, for example designated by B which has a higher energy level that of the orbital A is dropped into the orbital A. In some cases where the photon is generated and in other cases where the electron along the orbital, designated by C, for example, which has a higher energy level than that of the orbital A due to the Auger effect (hereinafter referred to as the Auger electron in the present invention). The energy and the number of the Auger electrons emitted to the outside of the surface are analyzed to thereby determine the three dimensional coordinate of the atomic nucleus of one atom of the surface, analyze the element thereof and analyze the chemical bond condition. As a result, it is possible to observe the atomic nucleus image including the element and chemical bond information (or it is possible to observe the element and chemical information of one atom which is to be a probe at the end of the probe in case of the probe). At the same time, it is also possible to observe the atomic order image through the conventional scanning type probe microscope.

Also, the energy and the number of the photons emitted to the outside of the surface are analyzed to thereby determine the three dimensional coordinate of the atomic nucleus of one atom of the surface, analyze the surface distribution concerning the element thereof and analyze the chemical bond condition. As a result, it is possible to observe the atomic nucleus image including the element and chemical bond information (or it is possible to observe the element and chemical information of one atom which is to be a probe at the end of the probe in case of the probe). At the same time, it is also possible to observe the atomic order image through the conventional scanning type probe microscope.

Also, it is preferable that the super short pulse high voltage has such a pulse width and a voltage that neither atom at the end of the probe nor atom on the surface of the sample is moved nor electric field evaporated and the photon or the Auger electron is discharged to the outside of the surface of the sample; and is set at such a high voltage of about several tens of kV to several tens of V that a time width of a half-cycle of a sine curve within the pulse in case of AC and a pulse width in case of DC are less than about several hundred of ps. Namely, if the super short pulse high voltage has such a pulse width and a voltage and is set at such a high voltage of about several tens of kV to several tens of V that a time width of a half-cycle of a sine curve within the pulse in case of AC and a pulse width in case of DC are less than about several hundred of ps, it is possible to discharge the photons and Auger electrons to the outside of the surface of the sample under the condition that neither atom at the end of the probe nor atom on the surface of the sample is moved nor electric field evaporated.

In this case, the "high voltage" in the present invention means the voltage that is much higher than the vias voltage of the several V in the regular scanning type tunnel microscope. The voltage is in the range of several tens of V to several tens of kV. The voltage is selected in response to the energy level of the electron orbital to be excited or the kind of the element forming the probe or the sample. Also, the "super short pulse" in the present invention means the pulse having a very short length of a time width only during which the high voltage may be applied without causing the atom to be electric evaporated.

Of the Auger electrons discharged to the outside of the surface of the sample and the probe, the Auger electron which has passed through an interval between a cone defined by a straight line having a small angle e relative to the surface of the sample and a surface substantially flush with the surface of the sample, passing through a point on the surface of the sample immediately below the atom of the end of the probe is analyzed by an energy analyzing counter, or of the photons discharged to the outside of the surface of the sample and the probe, the photon which has passed through an interval between a cone defined by a straight line having a small angle e relative to the surface of the sample and a surface substantially flush with the surface of the sample, passing through a point on the surface of the sample immediately below the atom of the end of the probe is analyzed by an energy analyzing counter. Namely, in the angular range between the cone defined by the straight line having the small angle θ, preferably, about less than 20°, relative to the surface of the sample and the surface substantially flush with the surface of the sample, passing through a point on the surface of the sample immediately below the atom of the end of the probe, the Auger electron and the photon which are generated from the atoms located in the lower layers than the surface layer are absorbed by the solid interior. For this reason, it is possible to obtain the information only concerning the real atom just below the surface by analyzing the Auger electron or the photon which has passed through this angular range with the energy analyzer.

On the other hand, another probe to be measured and used in the scanning type probe microscope is used as the sample, a three-dimensional coordinate of the atomic nucleus for one atom on the surface around the probe atom of the end of the probe to be measured, the element analysis thereof and the chemical bond condition analysis are conducted, and a three-dimensional image around the end of the probe to be measured and an atomic image including the element and chemical bond information are observed to thereby evaluate the probe to be measured.

Also, an atomic array of the probe to be machined and cooled, heated or kept at room temperature is measured by the measurement probe which may observe the atomic image and is heated, cooled or kept at room temperature by using the scanning type probe microscope, namely, after the atomic image of the probe is observed by the probe, or while observing the atomic image, the atom to be removed from the probe to be machined, the atom to be added thereto, the atom to be moved and the like are determined, a pulse having a suitable width, a suitable voltage and a polarity is once or repeatedly applied between the two probes, and the above-mentioned determined atom is removed, added or moved so as to stably project one atom at the end of the probe to be machined to thereby manufacture a sharp probe having one atom at the end, or the surface of the sample is analyzed by using the probe having one atom at the end.

The thus produced probe is very sharp with a radius of curvature at the end being about 5 Å, and is very stable and the state of the atom and the electron at the end may be well recognized. This probe is an ideal one for observing the atomic image. Also, in the element analyzing method with the scanning type probe microscope according to the present invention, the high voltage is applied between the probe and the sample. However, when the high voltage is applied between the probe and the sample, the orbital of the Auger electron generated from one atom immediately below the probe is curved by the electric field between the probe and the sample. If the average radius of curvature of the end of the probe is several hundred of Å, the electrons are dropped many times to the surface of the sample between the sample and the probe, so that almost no electrons reach the electron energy analyzer. Accordingly, the very sharp probe with the average radius of curvature at the end being 5 Å (from several tens of Å to the several Å) is inevitable for determining the atomic coordinate, the element analysis and the chemical bond condition analysis by the Auger electron spectroscopic.

Also, a goniometer having a rotary center around the end of the probe to be measured, a rotary stage, an XYZ stage and a data processing computer are used for adjusting the surface of the probe to be measured and the probe to be machined so as to be perpendicular to the measurement probe.

According to a second aspect of the invention, there is provided a super short pulse high voltage applying method in a scanning type probe microscope, characterized in that a DC or AC super short pulse high voltage is applied to a coaxial cable from a pulse power source in order to apply the super short pulse high voltage between a probe of the scanning type probe microscope and a sample, a terminal of the coaxial cable is connected to one of the probe and the sample; and the other side is kept substantially at an earth potential; an outer conductive sheath of the coaxial cable is cut at the terminal and a core line is exposed to be short as much as possible so that the terminal of the coaxial cable may be regarded as an open end; the core line is connected to one of the probe and the sample; and a super short pulse high voltage that becomes twice as much as the first-mentioned super short pulse high voltage due to a power reflection at the open end of the coaxial cable is applied between the probe and the sample without causing any strain to its waveform. According to the present invention, it is possible to determine the three dimensional coordinate of the atomic nucleus for every one atom of the surface, analyze the element thereof and analyze the chemical bond condition.

According to a third aspect of the invention, there is provided a super short pulse high voltage applying method in a scanning type probe microscope, characterized in that a DC or AC super short pulse high voltage is applied to a coaxial cable from a pulse power source in order to apply the super short pulse high voltage between a probe of the scanning type probe microscope and a sample, a terminal of the coaxial cable is connected to one of the probe and the sample; and the other side is kept substantially at an earth potential; an outer conductive sheath of the coaxial cable is cut at the terminal and a core line is exposed to be short as much as possible so that the terminal of the coaxial cable may be regarded as an open end; the core line is connected to one of the probe and the sample; a super short pulse high voltage that becomes twice as much as the first-mentioned super short pulse high voltage due to a power reflection at the open end of the coaxial cable is applied between the probe and the sample without causing any strain to its waveform; and at the same time, a bias voltage is superposed to the super short pulse high voltage or the earth potential is used as the bias potential. According to the present invention, it is possible to determine the three dimensional coordinate of the atomic nucleus for every one atom of the surface, analyze the element thereof and analyze the chemical bond condition while observing the atomic image by the regular scanning type probe microscope.

Thus, the super short pulse high voltage applying method in the scanning type probe microscope, is characterized in that a DC or AC super short pulse high voltage is applied to a coaxial cable from a pulse power source in order to apply the super short pulse high voltage between a probe of the scanning type probe microscope and a sample, a terminal of the coaxial cable is connected to one of the probe and the sample; and the other side is kept substantially at an earth potential; an outer conductive sheath of the coaxial cable is cut at the terminal and a core line is exposed to be short as much as possible so that the terminal of the coaxial cable may be regarded as an open end; the core line is connected to one of the probe and the sample; and a super short pulse high voltage that becomes twice as much as the first-mentioned super short pulse high voltage due to a power reflection at the open end of the coaxial cable is applied between the probe and the sample without causing any strain to its waveform. Namely, the terminal of the coaxial cable is regarded as the open end, and the core line is connected to the probe or the sample, it is possible to apply the high voltage transferred to the coaxial cable between the probe and the sample with high efficiency without deforming the waveform and with suppressing the radiation of electromagnetic wave from the core line as much as possible.

According to the present invention, the super short pulse high voltage is repeatedly applied to the probe or the sample to thereby excite the internal shell electron of the sample or the probe by the high energy electron projected from the probe or the sample (spherical symmetrically distributed valence electrons about the nucleus in some cases). When the electron having a higher energy level than that of the internal shell electron is dropped into the void produced by the excitation, the photon or Auger electron is emitted. However, the energy analysis and the counting analysis for the photons and the Auger electrons are carried out; that is, the information of the internal shell electrons or the like distributed in the spherically symmetric manner about the atomic nucleus is analyzed for every one atom so that it is possible to determine the three dimensional coordinate of the atomic nucleus for every one atom of the surface, analyze the element thereof and analyze the chemical bond condition.

Also, it is preferable that by utilizing such a phenomenon that a photon discharged from one of the probe or the sample is repulsively dispersed at the surface of the other at a certain probability, a maximum energy of the repulsively dispersed photon is analyzed by an electron energy analyzer, and a maximum voltage of the super short pulse high voltage applied between the probe and the sample is measured.

Also, it is preferable that by utilizing such a phenomenon that a photon discharged from one of the probe or the sample is braked and radiated at a certain probability when the electron discharged emitted from one of the sample and the probe is collided to the surface of the other of the sample and the probe, a maximum energy of the photon is analyzed by an electron energy analyzer, and a maximum voltage of the super short pulse high voltage applied between the probe and the sample is measured.

Then, in the second aspect of the invention, in order to repeatedly apply the AC super pulse high voltage between the probe and the sample, a pulse micro wave generated in a pulse magnetron is transferred in order of an attenuator for adjusting a power, a reflected power absorbing means for absorbing the reflected power and an adjustment means for matching an impedance, and the AC super short pulse high voltage is fed to the coaxial cable through a coaxial waveguide convertor for converting the transfer line from the waveguide for constituting the attenuator, the reflected power absorbing means and the adjustment means to the coaxial cable.

Also, in the third aspect of the invention, in order to repeatedly apply the AC super short pulse high voltage between the probe and the sample, a pulse micro wave generated in a pulse magnetron is transferred in order of an attenuator for adjusting a power, a reflected power absorbing means for absorbing the reflected power and a adjustment means for matching an impedance, the AC super short pulse high voltage is fed to the coaxial cable through a coaxial waveguide convertor for converting the transfer line from the waveguide for constituting the attenuator, the reflected power absorbing means and the adjustment means to the coaxial cable, a chalk flange for DC-like insulation and a bias voltage applying circuit for applying a DC bias voltage are added to the coaxial waveguide convertor on the upstream side of the coaxial waveguide convertor.

In the case where the micro wave technology is applied to the generation and transfer of the above described super short pulse high voltage, a waveguide type isolator or a circulator and a dummy load are used in combination as the reflected power absorbing means, and a waveguide type E/H tuner or a three stab tuner is used as the adjustment means.

It is also preferable in the second aspect of the invention that in order to repeatedly apply the DC super pulse high voltage between the probe and the sample, the DC super short pulse high voltage generated by a DC super pulse high voltage repeating generator is transferred, in order, to an attenuator for adjusting the power, and a reflected power absorbing means for absorbing the reflected power, and the DC super short pulse high voltage is fed to the coaxial cable.

It is also preferable in the third aspect of the invention that in order to repeatedly apply the DC super short pulse high voltage between the probe and the sample, the DC super short pulse high voltage generated by a DC super short pulse high voltage repeating generator is transferred, in order, to an attenuator for adjusting the power, and a reflected power absorbing means for absorbing the reflected power, the DC super short pulse high voltage is fed to the coaxial cable, and that the DC bias voltage is applied by a DC bias voltage superposing function provided in the DC super short pulse high voltage repeating generator or a bias tee provided between the attenuator and the reflected power absorbing means and a bias voltage applying circuit.

Also, in the case where the technology of the coaxial transfer line path is used to the transfer of the DC super short pulse high voltage, a waveguide type isolator or a circulator and a dummy load are used in combination as the reflected power absorbing means.

Thus, the super short pulse high voltage applying method in the scanning type probe microscope according to the present invention, by using as the power source the super short pulse high voltage repeating generator such as a pulse magnetron, and by using an isolator (which may be a circulator or a dummy load), an attenuator, an E/H tuner (or a three stab tuner or the like), a chalk flange (or a bias tee or the like), a coaxial waveguide convertor, and a coaxial cable, the terminal of the coaxial cable is machined to be an open end at which the power is substantially reflected, and the core line (conductor) of the coaxial cable is shortened as much as possible and connected to the probe (or sample). The reason why the core line is shortened at the terminal of the coaxial cable as much as possible is that since the super short pulse is used and the radiation of electromagnetic wave is very strong, the electromagnetic wave radiation must be reduced as much as possible, and the maximum super short pulse high voltage is applied to the probe (or sample). For the same reason, the part of the probe (or sample) is shortened as much as possible.

There is no method for directly measuring the super short pulse high voltage waveform applied to the probe (or sample). However, by utilizing the phenomenon that the high energy electron emitted from the probe (or sample) is repulsively dispersed at a certain probability at the surface of the sample (or probe), the energy analysis of the repulsive dispersed electron is performed by the electron energy analyzer. It is possible to know the maximum voltage of the super short pulse high voltage applied to the probe (or sample). Also, when the high energy electron emitted from the probe (or sample) is collided against the surface of the sample (or probe), the photon is emitted with a certain probability due to the brake radiation. The energy analysis of the photon is performed in the photon energy analyzer. It is possible to know the maximum voltage of the super short pulse high voltage applied to the probe (or sample) according to the maximum energy thereof.

If the super short pulse high voltage may be repeatedly applied to the probe (or sample), and if the energy analysis and the counter analysis of the photon or Auger electron excited by one atom on the surface of the sample (or probe) is performed in combination with the scanning type probe microscope due to the projection of the pulse high energy electron emitted by the application, it is possible to determine the three dimensional coordinate of the atomic nucleus for every one atom of the surface, analyze the element thereof and analyze the chemical bond condition.

DESCRIPTION OF THE PREFERRED EMBODIMENTS

According to the present invention, after the observation of an atomic order image through a conventional scanning type probe microscope or during the observation of the atomic order image, a high space resolving power of the scanning type probe microscope and an element analysis and a chemical bond condition analysis through an energy analysis of photons generated by high energy electron energy or an Auger electron spectroscopic method are combined with each other, to thereby determine the three dimensional coordinate of the atomic nucleus of one atom of the surface, analyze the element thereof and analyze the chemical bond condition for proving an element analyzing method and a super short pulse high voltage applying method in the scanning type probe microscope for observing the atomic nucleus image including the element and chemical bond information.

Figure 1:
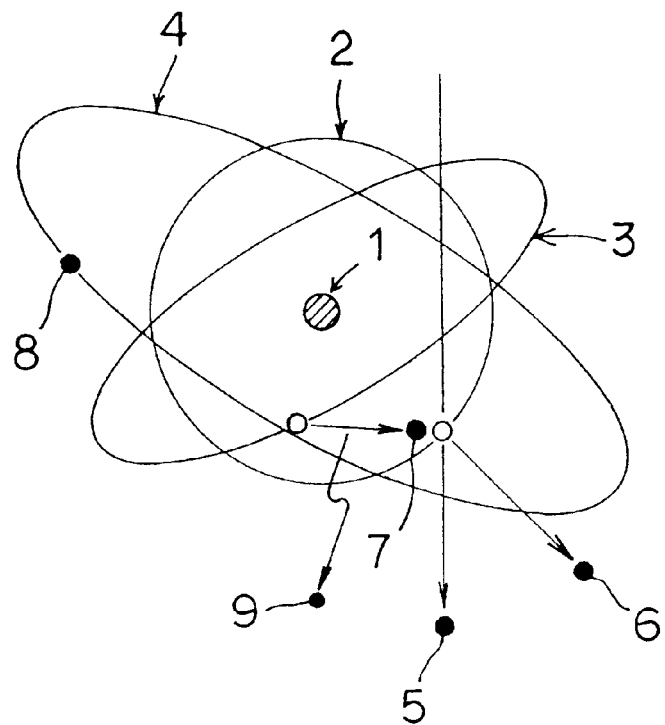
FIG. 1 is an illustration of a principle of the photon being discharged from the solid surface by a high energy electron projection.
Figure 2:
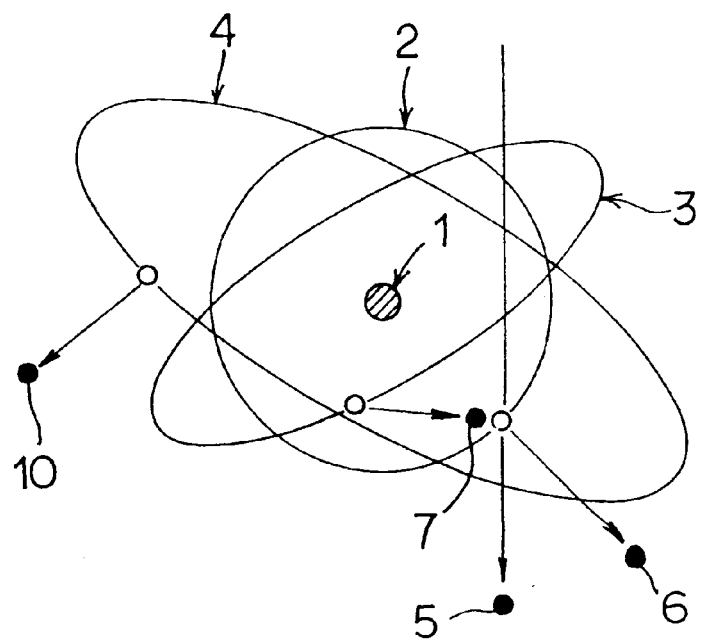
FIG. 2 is an illustration of a principle of the Auger electron being discharged from the solid surface by a high energy electron projection.

The present invention will now be described on the basis of the embodiments shown in the accompanying drawings in more detail. FIG. 1 graphically illustrates a principle in which a photon is generated when a high energy electron is projected to an atom. In FIG. 1, reference numeral 1 denotes an atomic nucleus, reference numeral 2 denotes an orbital A of an internal shell electron (which may be a valence electron in some cases), reference numeral 3 denotes an orbital B having a higher energy level than that of the orbital A, reference numeral 4 denotes an orbital C having a higher energy level than that of the orbital A, reference numeral 5 denotes a high energy electron projected from the outside, reference numeral 6 denotes an excited electron of the orbital A, reference numeral 7 denotes an electron dropped from the orbital B to the orbital A, reference numeral 8 denotes an electron of the orbital C, and reference numeral 9 denotes a photon which is generated when the electron is dropped from the orbital B to the orbital A. FIG. 2 graphically shows a principle of the generation of the Auger electron when the high energy electron is projected to the atom. In FIG. 2, reference numeral 10 denotes an Auger electron emitted from the orbital C when the electron is dropped from the orbital B to the orbital A.

Figure 3:
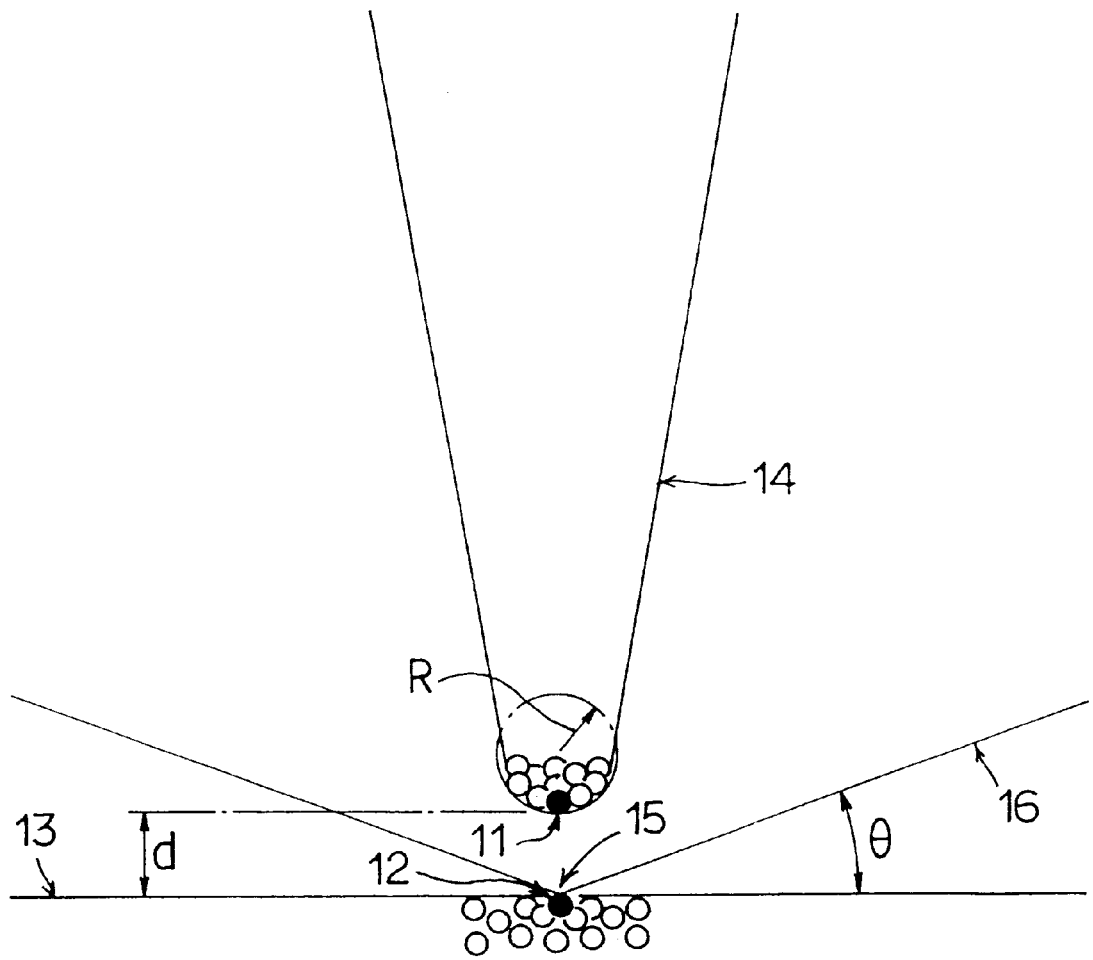
FIG. 3 is an illustration of a measurement principle in a scanning type probe microscope.

FIG. 3 denotes a measurement principle according to the present invention. A distance d between an end probe atom 11 of a scanning type probe microscope and a sample surface atom 12 located immediately below the probe atom 11 is set at an extremely short distance (ideally about 1 nm). During the inherent operation of the scanning type probe microscope or in stopping the operation, a super short pulse high voltage of AC or DC is once or repeatedly applied between the surface of the sample 13 (which is cooled down to about 77 K to 4.2 K in some cases) and the extremely sharp and thin probe 14 (which is cooled down to about 77 K to 4.2 K in some cases) in the form of a conical shape, using one end atom as the probe atom, or after the pulse high voltage has been applied, the probe and the sample surface are moved relatively each other to thereby perform the scanning operation. In this case, a pulse width and voltage level of the above-described super short pulse high voltage is determined in view of the following factors. Namely, only the tunnel current is allowed to flow, and in order to prevent the end probe atom and the surface atom from electric field evaporating, a time width w of half a cycle of sine wave within the pulse is reduced down to a pulse width number of about 100 ps or less as much as possible in case of AC, and it is reduced down to a pulse width number of about 100 ps or less as much as possible in case of DC. Thus, to excite the internal shell electron (which may be a valence electron in some cases) and to emit the Auger electron or the photon, the high voltage of several tens of kV to several tens of V is applied. Ideally, the high energy electron is projected to one surface atom or one probe atom.

In this case, the high energy electron emitted from the probe 14 (or from the sample surface atom) is expanded only substantially over one atom of the surface of the sample 13 (or the end of the probe). (In this case, the deep portion of the third or more layers of the surface is excluded.) Ideally, the internal shell electron (which may be the valence electron in some cases) of the orbital 2 referenced by, for example, A of one surface atom 12 (or one end probe atom 11 just above the sample surface atom) just below the end probe atom is excited. Then, the electron of the orbital 3 referenced by, for example, B which has a higher energy level than that of the orbital A of the excited atom is dropped to the orbital A. At this time, there are some cases where the photon 9 is generated and there are the cases where the electron in another orbital 4 referenced by, for example, C and which has a higher energy level than that of the orbital A due to the Auger effect. Of the generated photons 9 or the Auger electrons 10, the energy analysis is applied to one that has passed close to a point 15 on the sample surface immediately below the probe and has passed between a cone 16 defined by a small angle θ (about 20° or less) relative to the surface of the sample 13 and a plane 17 which is substantially flush with the surface of the sample 13 shown in FIG. 4 and that has emitted to the outside of the surface. (This condition is set for the purpose of inferring the atomic coordinate in the depth direction and obtaining only the information from the first atomic layer to the approximately second atomic layer, while absorbing and removing the photons or the Auger electrons generated from the lower layer atom than the surface atom by the interior of the solid substance.) Namely, the three-dimensional coordinate information of the energy analysis is considered in addition to the information only about the tunnel current or the interatomic force for the determination of the three-dimensional coordinate of the atomic nucleus, the element analysis and the chemical bond condition analysis for every one surface atom.

Incidentally, when the potential of the probe 14 is kept at zero, and the DC super short pulse high voltage is applied to the sample 13 in the same way as described above, ideally, the high energy electron emitted from one surface atom of the sample surface is projected to one probe atom of the probe end. Accordingly, ideally, the photon or Auger electron is emitted from one probe atom, the energy analysis of the photon or the Auger electron which has passed within the above-described small angle θ is carried out so that the element analysis and the chemical bond condition analysis may be effected for one probe atom.

Figure 4:
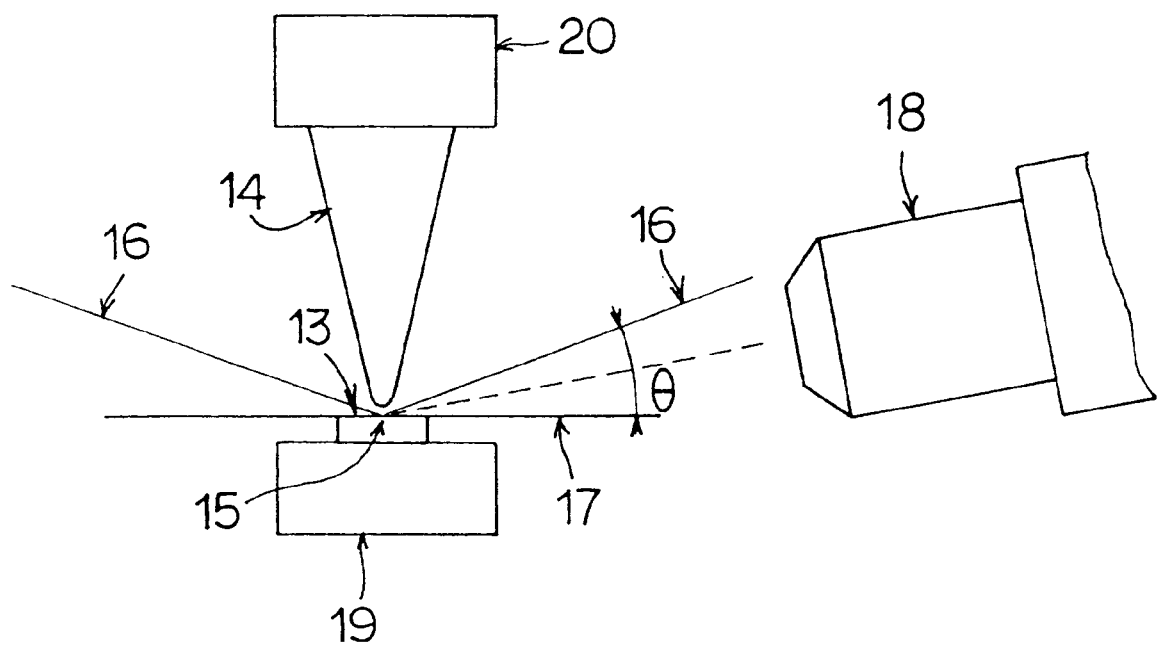
FIG. 4 is an illustration showing a positional relationship among a probe, a sample surface and an energy analyzing counter.

FIG. 4 shows a positional relationship among the probe 14, the surface of the sample 13 and the energy analyzing counter 18 of the electrons and photons. The energy analyzing device 18 may analyze the energy of the photon 9 or the Auger electron 10 emitted in the direction of the angle θ. In order to enhance the sensitivity, a plurality of analyzing devices may be arranged around the probe. Incidentally, in FIG. 4, reference numerals 19 and 20 denote coolers. Also, it is possible to measure the maximum voltage of the super short pulse high voltage applied between the probe 14 and the surface of the sample 13 by measuring the maximum energy of the electron repulsively dispersed at the surface or the photon generated due to the brake radiation of the projected electron.

Figure 5:
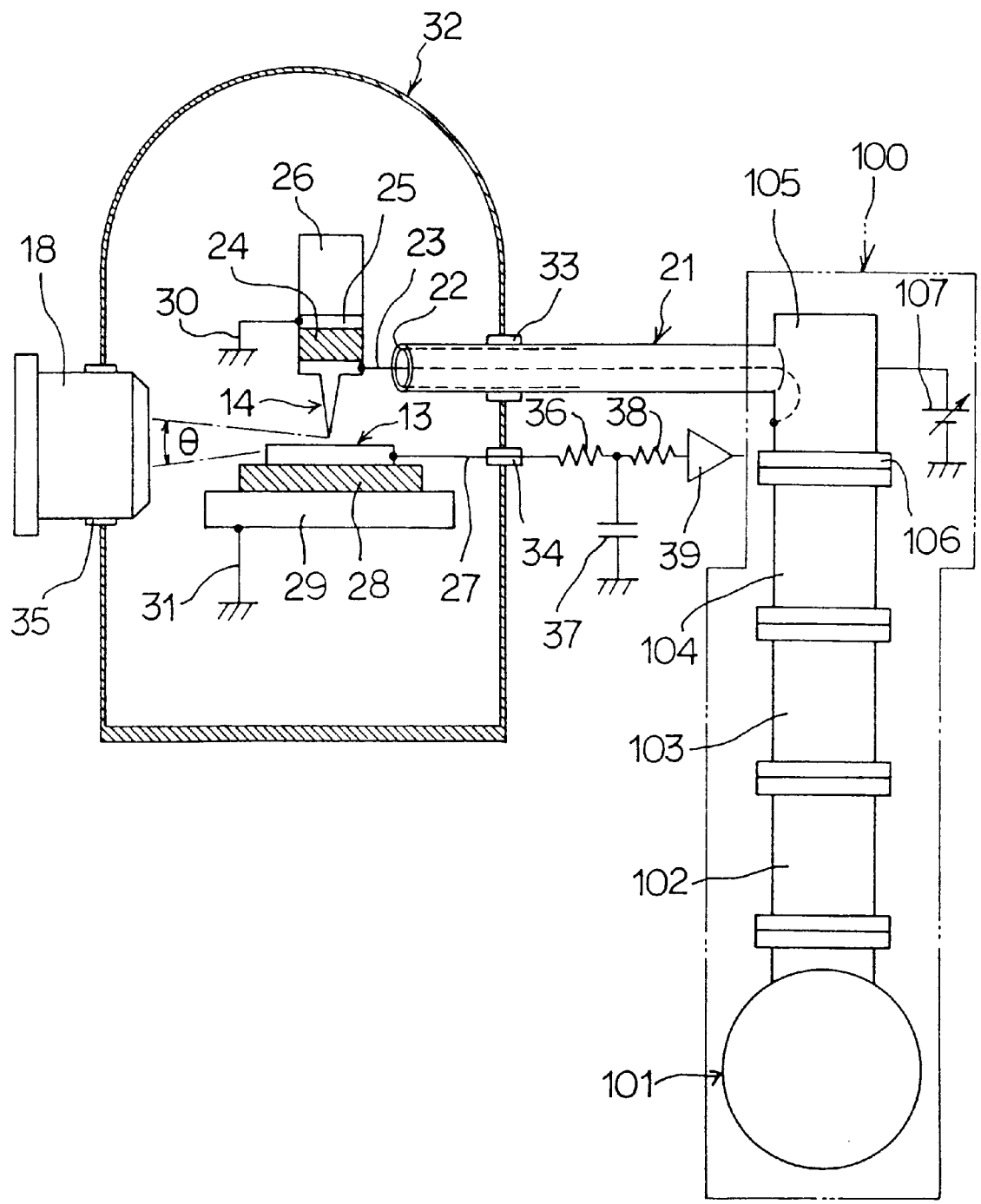
FIG. 5 is an illustration of an AC super short pulse high voltage applying method.

The embodiment shown in FIGS. 5 and 6 will now be described in detail. FIG. 5 shows how to apply the AC super short pulse high voltage between the probe 14 of the scanning type probe microscope and the sample 13. In order to suppress the radiation of the super short pulse high voltage as the magnetic wave radiation in the ambient space as much as possible, the probe 14 is shorten as much as possible. The embodiment shows an example of applying the super short pulse high voltage to the probe 14 but it is possible to apply it to the sample 13. With respect to a semi-rigid coaxial cable 21 used as a transfer line for feeding the AC super short pulse high voltage from an AC super short pulse high voltage generating system 100, an outer sheath of the coaxial cable 21 is cut at the terminal and a core member 23 is exposed to be as short as possible so that the terminal may be regarded as an open end. Then, the core line 23 is connected to the probe 14, and a voltage that is twice higher than the super short pulse high voltage to be transferred through the coaxial cable 21 is applied between the probe 14 and the sample 13. In this case, since the exposed length of the core line 23 is shortened so that the terminal of the coaxial cable 21 may be regarded as the open end, the super short pulse high voltage transferred through the coaxial cable 21 is reflected at the open end to become the voltage which is twice as high as the super short pulse high voltage and to be applied to the probe 14. At the same time, a strain of the voltage wave at the open end, for example, such a strain that the pulse width is expanded is not generated. Furthermore, it is possible to suppress the radiation of the electromagnetic wave from the core line 23 to a minimum level. Incidentally, from the radiation reduction point of view, it is preferable to shorten the exposed length of the core line 23, as much as possible, to be ½ or less of the wavelength of the super short high voltage to be transferred through the coaxial cable. For example, in the case where a frequency of the super short pulse high voltage is 50 GHz, the exposed length of the core line 23 should not be greater than about 3 mm.

The above-described probe 14 is mounted on an XYZ piezoelectric scanner 26 through a metal shield plate 25 and an insulator 24 made of tetrafluoroethylene resin and is scanned along the surface of the sample 13. The capacitance of the insulator 24 made of tetrafluoroethylene resin is reduced as much as possible so that the super short pulse high voltage is not absorbed by the metal shield plate 25. On the other hand, the sample 13 is connected to a lead line 27 for measuring the tunnel current, and at the same time, is mounted to a sample table 29 through an electric insulator 28. In this case, an earth line 30 is connected to the metal shield plate 25, and an earth line 31 is connected also to the sample table 29. These components are kept at the earth potential, respectively. Then, the sample 13 and the probe 14 are disposed in the interior of a vacuum container 32. The above-described coaxial cable 21 and lead line 27 are connected to the probe 14 and the sample 13, passing through the vacuum container 32 through electric insulative vacuum shields 33 and 34, respectively.

Although the energy analyzing counter 18 is either electronic energy analyzing counter or photon energy analyzing counter but it is preferable to include both type devices. The energy analyzing counter 18 is mounted through an electric insulative vacuum shield 35 on the above-described vacuum container 32 with its detecting axis being directed in the surface tangential direction. Also, the entraining angle θ of the energy analyzing counter 18 for the electron or the photon is about 20°, and its detecting axis is preferably variable in the range of ±θ/2 in the vertical direction relative to the samples surface.

A high cut filter resistor 36 is connected in series with the lead line 27 for cutting the super short pulse current, and a high cut filter capacitor 37 is connected in parallel with the lead line 27 for cutting the super short pulse current. The tunnel current flowing through the lead line 27 is measured by a current amplifier 39 for the tunnel current amplification through an input resistor 38.

Also, in the AC super short pulse high voltage generating system 100, a super short pulse micro wave generated in a pulse magnetron 101 is fed to a waveguide in order to apply the AC super short pulse high voltage between the probe 14 and the sample 13 in a repeated manner. The power is adjusted through an attenuator 102. The super short pulse micro wave is transferred, in order, to an adjustment means 104 for impedance matching through a reflected power absorbing means 103 for absorbing the reflected power which comes back through a total reflection at the terminal of the coaxial cable 21. The AC super short pulse high voltage is fed to the above-described coaxial cable 21 through a coaxial waveguide convertor 105 for converting the transfer line to the above described coaxial cable 21 from the waveguide constituting the above-described attenuator 102, reflected power absorbing means 103 and adjustment means 104. Then, in order to apply the DC bias voltage to the above-described probe 14, a chalk flange 106 for the DC insulation and a bias voltage application circuit 107 for applying the DC bias voltage are added to the above-described coaxial waveguide convertor 105 on the upstream side of the coaxial waveguide convertor 105. In this case, a combination of a waveguide type isolator or a circulator and a dummy load is used as the above-described reflected power absorbing means 103. A waveguide type E/H tuner or a three stab tuner is used as the above-described adjustment means 104. Then, it is preferable to use the pulse magnetron 101 having a frequency of about 50 GHz or more and a peak output of about 50 kW.

Figure 6:
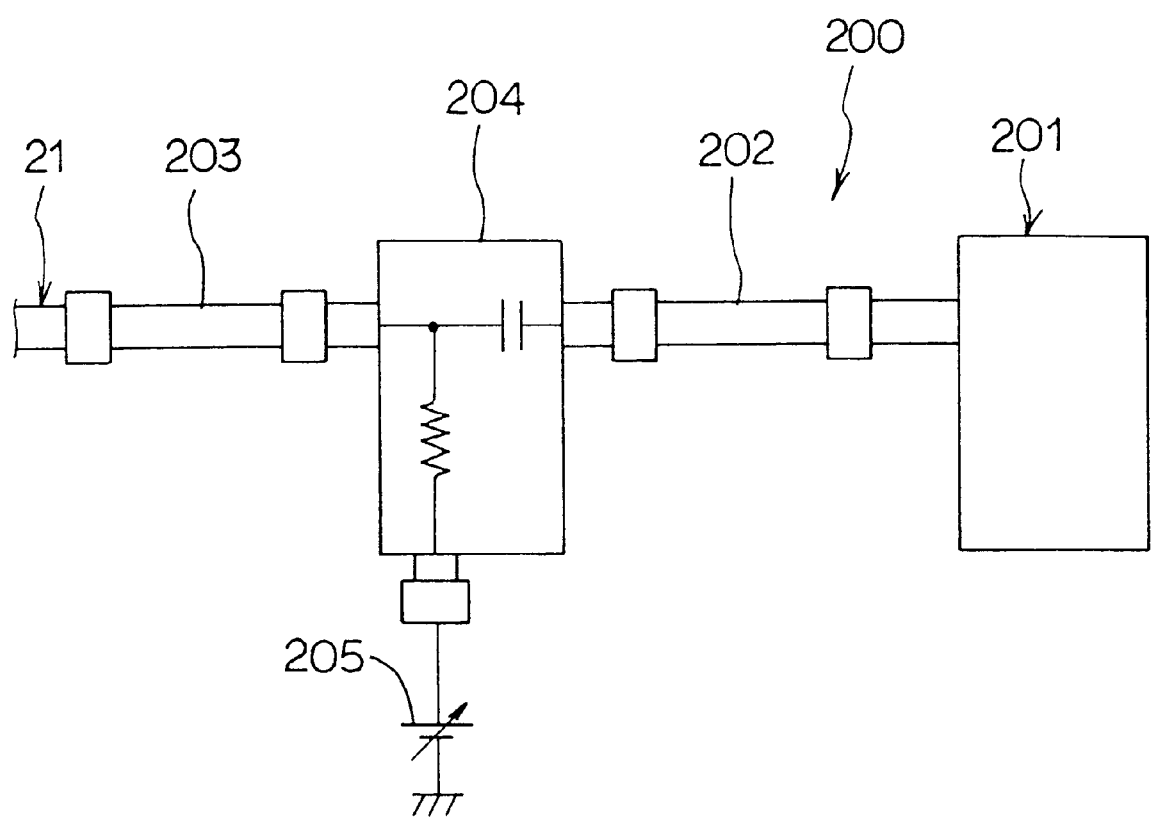
FIG. 6 is an illustration of an DC super short pulse high voltage applying method.

Also, FIG. 6 schematically shows how to apply the DC super short pulse high voltage between the probe 14 of the scanning type probe microscope and the sample 13. The part shown in FIG. 6 is directed to the DC super short pulse high voltage generating system 200, and the other structure is the same as described above. Therefore, the detailed explanation therefor will be omitted. The DC super short pulse high voltage generating system 200 supplies the coaxial transfer cable with the DC super short pulse high voltage generated in the DC super short pulse high voltage repeating generator 201. The power is adjusted by an attenuator 202. Thereafter, the power is transferred, in order, to the reflected power absorbing means 203 for absorbing the reflected power that is totally reflected at the terminal of the coaxial cable 21. The DC super short pulse high voltage is fed to the coaxial cable 21. In this case, a coaxial type isolator or a circulator and a dummy load are used in combination as the reflected power absorbing means. Also, in order to apply the DC bias voltage to the probe 14, the DC bias voltage is superposed and applied to the DC super short pulse high voltage by the DC bias voltage superposing function provided in the above-described DC super short pulse high voltage repeating generator 201, or the DC bias voltage is superposed and applied to the DC super short pulse high voltage by a bias means 204 interposed between the attenuator 202 and the reflected power absorbing means 203 and a bias voltage applying circuit 205 added thereto. Incidentally, if the above-described DC super short pulse high voltage repeating generator 201 is provided with the DC bias voltage superposing function, the bias means 204 and the bias voltage applying circuit 205 may be dispensed with. it is preferable to use the DC super short pulse high voltage repeating generator 201 that has a pulse width of about 100 ps or less and a peak voltage of about 2 kV or more.

Figure 7:
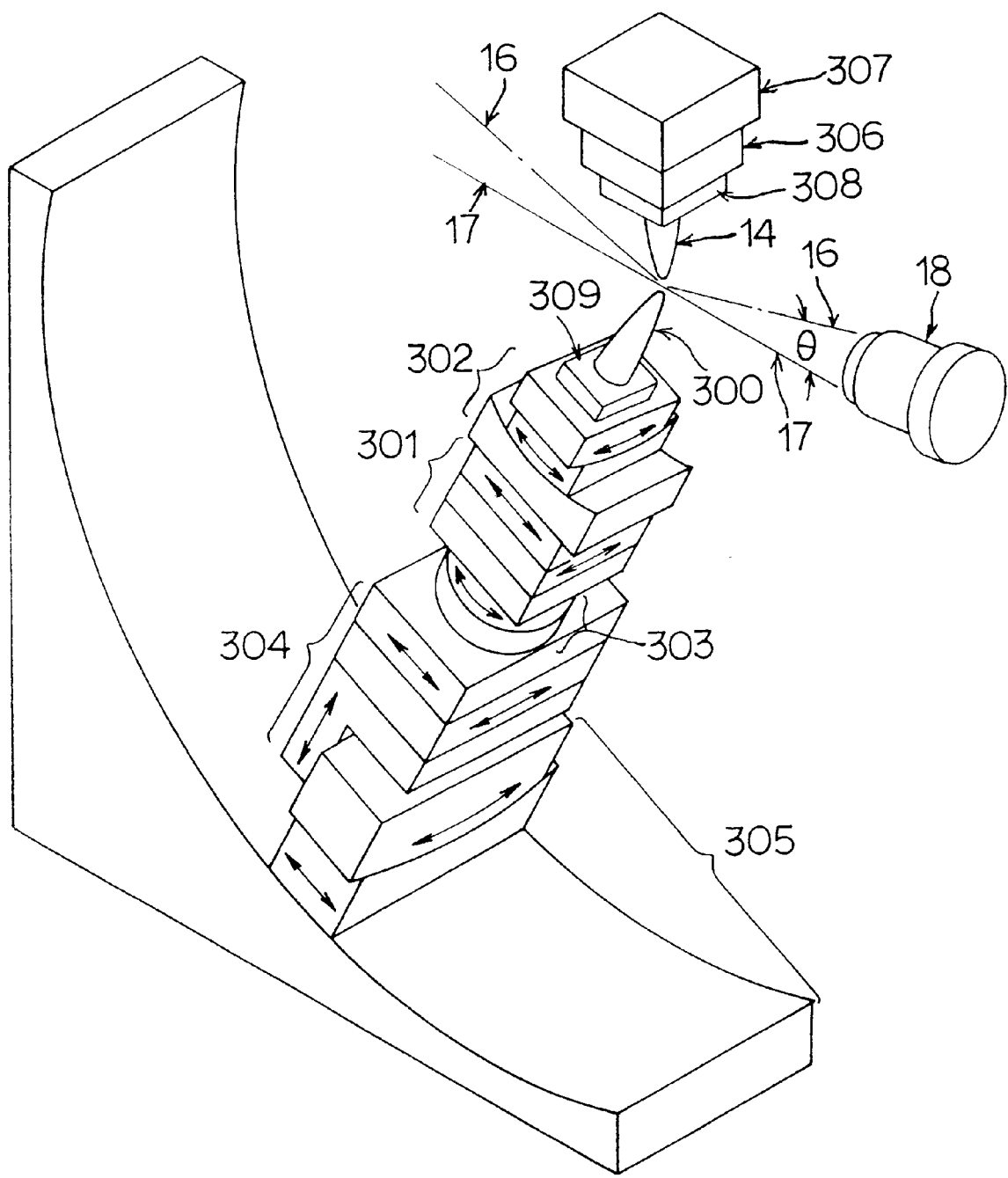
FIG. 7 is a schematic perspective view showing a device for machining a probe, to be measured, in an atomic unit to be a very sharp probe with a radius of curvature of 5 Å at the end and observing a probe atom at the end of the probe to be measured by the scanning type probe microscope.

FIG. 7 shows, as another operational condition of the element analyzing method with the scanning type probe microscope, a case where another separate probe 300 to be measured instead of the surface of the sample 13 facing the probe 14 as the detecting probe is provided as the sample; that is, an outline of the method for the determination of the three-dimensional coordinate of the atomic nucleus, the element analysis and the chemical bond condition analysis for one surface atom, in which the probe 300 to be measured is measured by the probe 14, further the AC or DC super short pulse high voltage is applied between the probe 14 and the probe 300 to be measured in the same manner as described above, and the energy of the photon 9 or the Auger electron 10 that has passed within the small angle θ is analyzed. Namely, the probe 300 to be measured is mounted substantially vertically on a bi-axial goniometer 302 mounted on an XY stage 301, and the XY stage 301 and the bi-axial goniometer 302 are finely adjusted whereby the centerline of the substantially conical probe 300 to be measured is caused to be identical with a rotational centerline of a rotary stage 303. Subsequently, an XYZ stage 304 is finely adjusted, so that the position of the probe end atom of the probe 300 to be measured is caused to be identical with the center of rotation of a bi-axial goniometer 305. Thereafter, the probe 14 is moved close to the probe end atom of the probe 300 to be measured by an XYZ piezoelectric scanner 306 and an XYZ stage 307 therefor. (In this case, the bi-axial goniometer 305 and the rotary stage 303 are finely adjusted so that the surface of the probe 306 to be measured is normally substantially perpendicular to the central axis of the probe 14).

Then, in the operational mode of the conventional scanning type probe microscope, a three-dimensional image of the probe 300 to be measured in the range of several 100 nm and the atomic array around the probe end atom of the probe 300 to be measured is computer processed and formed into an image on the basis of the positional information of the rotary stage 303, the XYZ stage 304, the bi-axial goniometer 305, the XYZ piezoelectric scanner 306, the XYZ stage 307 and the like. At the same time, in the element analyzing method with the scanning probes microscope using the energy analyzing counter 18 for the photon or the Auger electron, the determination of the three-dimensional coordinate for the atomic nucleus, the element analysis and the chemical bond condition analysis for one surface atom around the probe end atom of the probe 300 to be measured are carried out and the computer process is used for imaging the information. Furthermore, the three-dimensional image including the three-dimensional coordinate and the element analysis information of the atomic nucleus of the probe 300 to be measured in the range of several hundred nm around the probe end atom is computer processed and is formed into an image. In this case, it is possible to observe the image with the probe 14 and the probe 300 to be measured being cooled by the heating or cooling device 308 and the heating or cooling device 309, respectively.

Figure 8A:
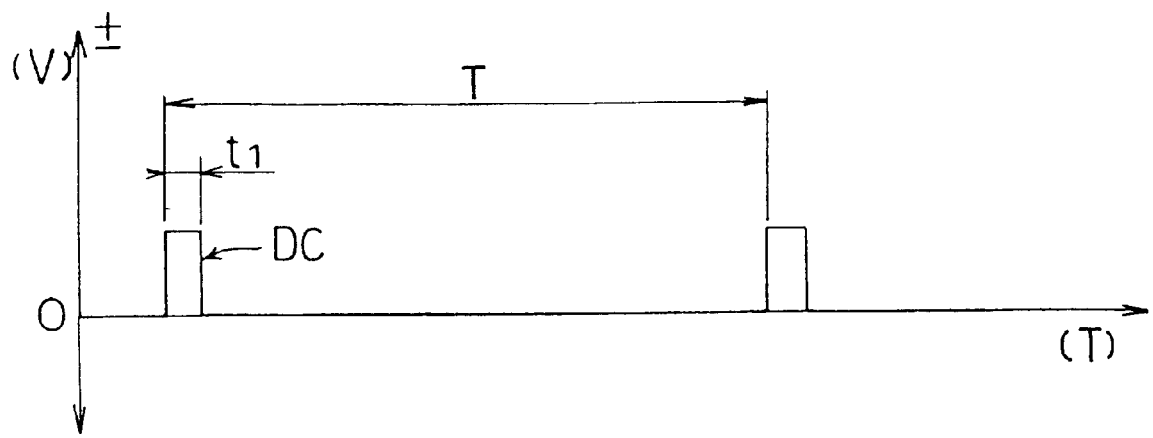
FIG. 8(a) is a diagram showing a DC waveform of the super short pulse high voltage applied between the probe and the sample.
Figure 8B:
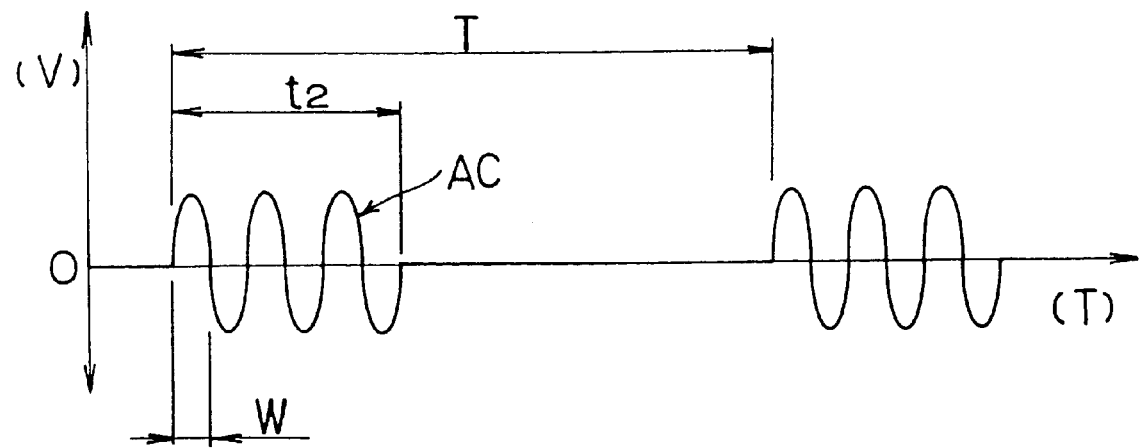
FIG. 8(b) is a diagram showing an AC waveform of the super short pulse high voltage applied between the probe and the sample.

FIG. 8(a) shows a waveform of the DC super short pulse high voltage applied between the probe 14 and the surface of the sample 13 (or the probe 300 to be measured), where $t_1$ is the pulse time width (preferably about several hundred ps or less), and T is the repeated time interval, In case of the DC super short pulse high voltage, either plus or minus polarity may be used for the voltage. FIG. 8b) shows a waveform of the AC super short pulse high voltage applied between the probe 14 and the surface of the sample 13 (or the probe 300 to be measured) in the same manner. Also in case of the super short pulse high voltage, either plus or minus polarity may be used for the voltage. It is sufficient that the number of the sine curves within one AC super short pulse is at least one (it is preferable that the half-cycle time w is about several hundred ps or less). The time width $t_2$ of the AC super short pulse is about several hundred ns or less. The shorter the time width, the better the effect will become. The duty $t_1/T$ or $t_2/T$ is reduced as much as possible so that the S/N ratio may be kept at a minimum possible limit.

Figure 9A:
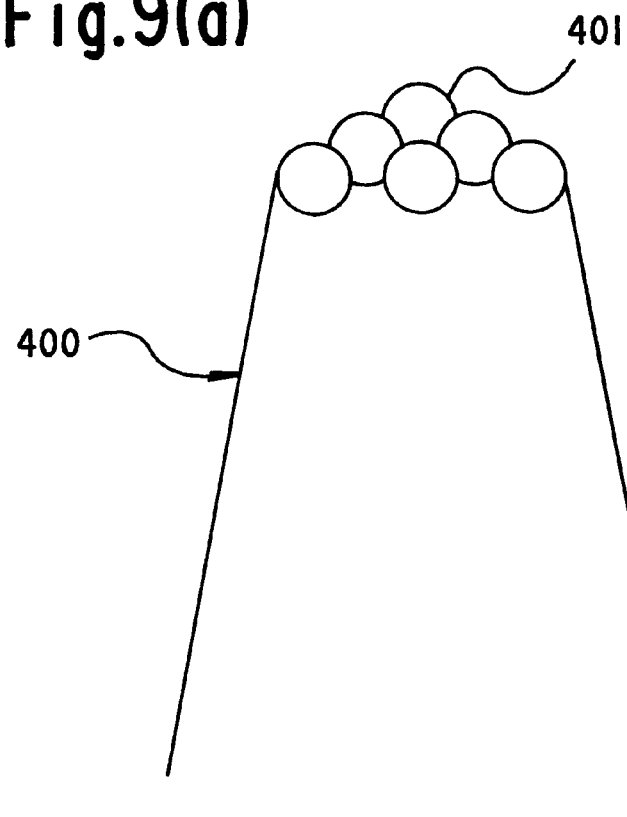
FIG. 9(a) is a schematic side elevational view showing a probe of one atom at the end which may be produced in an atomic unit machining.
Figure 9B:
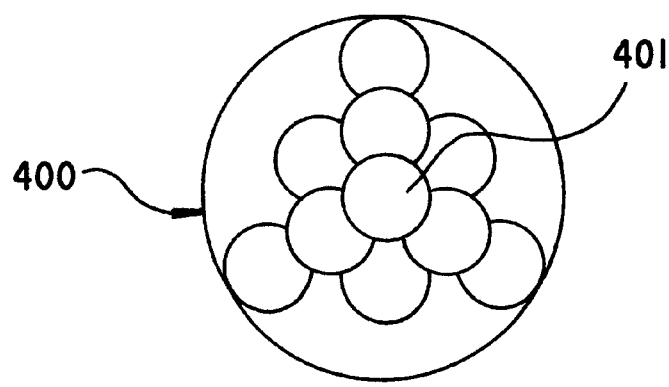
FIG. 9(b) is a schematic frontal view thereof.

Finally, a method for producing the foregoing probes will now be explained briefly. In general, the probe is produced by mechanical polishing, electrolyte polishing or electric field evaporation within an electric field ion microscope so that the probe is sharp in an atomic level. A radius of curvature of an end of the probe thus produced is about 100 Å or more. This is not said to be sufficiently sharp. A mini-chip is present at the end of the probe. This only means that one atom is accidentally projected slightly to be probe atom. Accordingly, not depending upon the accidental probability, the invention provides the method for always producing the probe with stability and good reproductivity. To meet this, first of all, the atomic array around the end of the probe to be machined and the three-dimensional image in the range of several hundred nm are imaged by observing through the apparatus shown in FIG. 7. On the basis of the result, the atom to be removed from the probe end of the probe to be machined, the atom to be added and the atom to be moved are determined. Subsequently, while observing the atomic image of the probe to be measured (corresponding to the probe 300 to be measured) by the probe for measurement (corresponding to the probe 14), the pulse voltage of several V and several tens of ms is once or repeatedly applied between both the probes by using the positive and negative pulse power sources so that the probe is machined in an atomic unit by the electric evaporation or the like. The setting of heating, cooling or a room temperature for the measurement probe and the probe to be machined is carried out by the heating and cooling devices 308 and 309. Which setting should be selected is determined by a kind of atomic unit machining including the polarity of the voltage. This operation is repeated, and the atomic array w <111> is selected as the axial orientation as designed and as shown in FIGS. 9(a) and 9(b) to thereby produce the probe 400 of one atom at the end.

The thus produced probe becomes one atom end probe which is very sharp in the level of the average end curvature radius R of several tens of Å to several Å and which is thin, conical and stable. If this probe is used as the probe for the element analysis with the scanning type probe microscope, it is possible to observe and measure a variety of aspects for every one atom of the surface of the sample with a high resolving power. In particular, in the element analysis with the scanning type probe microscope according to the present invention, the high voltage is applied between the probe and the sample. Therefore, the very sharp probe having the average curvature radius of the end at about 5 Å (several tens of Å to several Å) is inevitable to determine the atomic coordinate, analyze the element, and analyze the chemical bond condition by the Auger electron spectroscopic analysis. This is because, if the high voltage is applied between the probe and the sample, the orbital of the Auger electron generated from one atom just below the probe is curved by the electric field between the probe and the sample, and if the average radius of curvature of the end of the probe is large to be several hundred Å as in the conventional case, the electron is a number of times dropped to the sample surface between the probe and the sample so that the electron could not reach the electron energy analyzing apparatus.

The method which may perform the most minute area/polarity surface layer analysis among the conventional element analysis and chemical bond condition analyzing technology is a scanning type Auger electron spectroscopic analysis. Even by the up-to-date technique, the measurement range is several tens of nm in diameter and several nm in depth. It is impossible to measure the surface atom one by one. On the other hand, with a scanning type tunnel microscope and an atomic interactive force microscope, it is possible to perform the real space resolving power in the atomic order. It is however not always easy to perform the interpretation of the measurement result. In many cases, it is difficult to determine the atomic coordinate. Needless to say, it is impossible to conduct the element analysis and the chemical bond condition analysis for every one atom on the surface with the state of the art.

In the element analyzing method with the scanning probe microscope according to the present invention, it is possible to determine the three dimensional coordinate of the atomic nucleus of one atom of the surface, analyze the element thereof and analyze the chemical bond condition which have been impossible in the state of the art.

Also, in the super short pulse high voltage applying method with the scanning type probe microscope according to the present invention, it is possible to repeatedly apply the AC or DC super short pulse high voltage of a peak voltage of several tens of V to several tens of kV and of a pulse width of about several hundred ps or less between the probe and the sample.

Namely, according to the present invention, the high space resolving power of the scanning type probe microscope is combined with the element analysis and the chemical bond condition analyzing ability of the Auger electronic spectroscopic method, and the energy analyzing results of the Auger electron generated by the high energy electron projection are considered, whereby it is possible to determine the three dimensional coordinate of the atomic nucleus of one atom of the surface, analyze the element thereof and analyze the chemical bond condition. Also, in case of the combination with the energy analysis of the photon generated by the projection of the high energy, it is possible to determine the three dimensional coordinate of the atomic nucleus of one atom of the surface, analyze the element thereof and analyze the chemical bond condition.

In more detail, the super short pulse high voltage applying method according to the present invention, also, the energy analyzing counter for the photon and the Auger electron is incorporated into the system, further, and the probe having the radius of curvature of several tens Å to several Å at the end is used to form the new scanning type probe microscope. It is possible to repeatedly apply the super short pulse high voltage to the probe or the sample and to excite the internal shell electron of the sample or the probe by the high energy electron projected from the probe or the sample (spherical symmetrically distributed valence electrons about the nucleus in some cases). When the electron having a higher energy level than that of the internal shell electron is dropped into the void produced by the excitation, the photon or Auger electron is emitted. Accordingly, the energy analysis and counter analysis are carried out for the photon or the Auger electron; that is, the information of the internal shell electrons or the like spherically symmetrically distributed about the nucleus is analyzed for every one atom. It is thus possible to determine the three dimensional coordinate of the atomic nucleus of one atom of the surface, analyze the element and analyze the chemical bond condition. Namely, it is possible to know the information of the nucleus that could not be measured by the conventional scanning type probe microscope.

Thus, it is possible to inspect and specify the surface element distribution and the impurity element distribution in the atomic order in a silicon wafer, gallium arsenic wafer and a ULSI. The invention contributes to the development of the semiconductor industry. Also, the invention contributes to realizing atom craft by the atom maneuver, is available for the surface atomic structure analysis for contributing realization and discovering a mechanism of a high temperature super conductor, and is useful for the determination of the atomic nucleus array of DNA or the like in the life science, the element analysis and the chemical bond condition analysis, leads to a way to the replacement of DNA such as composition of new DNA, severing and combining DNA and contributes to the development of the biotechnology industry.

What we claim is:

1. An element analyzing method utilizing a scanning type probe microscope, in which a distance between an end of a probe and a sample is extremely shortened, during the inherent operation of the scanning type probe microscope or in stopping the operation thereof, comprising the steps of:

applying, at least once or repeatedly, a super short AC or DC high voltage pulse to the probe so as to generate an electric potential difference between the probe and the sample;

discharging an electron from the sample to the probe;

discharging a photon or an Auger electron from an atom of an end of the probe by an impact of the electron;

analyzing an energy and the number of photons and the number of electrons of the photons and the Auger electrons discharged to the outside of the atom of the end of the probe; and carrying out the element analysis thereof, and a chemical bond condition analysis.

2. An element analyzing method utilizing a scanning type probe microscope, in which a distance between an end of a probe and a sample is extremely shortened, during the inherent operation of the scanning type probe microscope or in stopping the operation thereof, comprising the steps of:

applying, at least once or repeatedly, a super short AC or DC high voltage pulse to the probe so as to generate an electric potential difference between the probe and the sample;

discharging an electron from the probe to the sample;

discharging a photon or an Auger electron from the sample by an impact of the electron;

after the super short high voltage pulse has been applied, moving the sample and the probe relative to one another to scan the surface of the sample with the probe to obtain an atomic order image of the surface of sample;

analyzing an energy and the number of photons and the number of electrons of the photons and the Auger electrons discharged to the outside of the surface from the sample; and carrying out a determination of three-dimensional coordinates of a nucleus for every atom of the surface of the sample, the element analysis thereof, and a measurement of a surface distribution concerning a chemical bond condition analysis to obtain an atomic image of the surface of the sample including element and chemical bond information.

3. The element analyzing method with a scanning type probe microscope according to either claim 1 or 2, wherein said super short high voltage pulse has a pulse width and a voltage such that neither atom at the end of the probe nor atom on the surface of the sample is moved nor electric field evaporated and the photon or the Auger electron is discharged to the outside of the surface of the sample; and is set at such a high voltage of about several tens of kV to several tens of V that a time width of a half-cycle of a sine curve within the pulse in case of AC and a pulse width in case of DC are less than about several hundred of ps.

4. The element analyzing method with a scanning type probe microscope according to claim 2, comprising the additional step of analyzing, by an energy analyzing counter, out of the Auger electrons discharged to the outside of the surface of the sample, the Auger electron which has passed through an interval between a cone defined by a straight line having a small angle $\theta$ relative to the surface of the sample and a surface substantially flush with the surface of the sample, passing through a point on the surface of the sample immediately below the atom of the end of the probe.

5. The element analyzing method with a scanning type probe microscope, according to claim 4, wherein the small angle $\theta$ relative to the surface of the sample is not greater than about 20°.

6. The element analyzing method with a scanning type probe microscope according to claim 2, comprising the additional step of analyzing by an energy analyzing counter, out of the photons discharged to the outside of the surface of the sample, the photon which has passed through an interval between a cone defined by a straight line having a small angle $\theta$ relative to the surface of the sample and a surface substantially flush with the surface of the sample, passing through a point on the surface of the sample immediately below the atom of the end of the probe.

7. The element analyzing method with a scanning type probe microscope according to claim 2, wherein another probe to be measured and used in the scanning type probe microscope is used as the sample, comprising the additional steps of:

conducting measurement of three-dimensional coordinates of the atomic nucleus for one atom on the surface of the end of the probe to be measured, the element analysis thereof and the chemical bond condition analysis; and observing a three-dimensional image around the end of the probe to be measured and an atomic image including the element and chemical bond information to thereby evaluate the probe to be measured.

8. The element analyzing method with a scanning type probe microscope, according to claim 7, a goniometer having a rotary center around the end of the probe to be measured, a rotary stage, an XYZ stage and a data processing computer are used for adjusting the surface of the probe to be measured and the probe to be machined so as to be perpendicular to the measurement probe.

9. The element analyzing method with a scanning type probe microscope according to claim 2, wherein an atomic array of the probe to be machined and cooled, heated or kept at room temperature is measured by the measurement probe which may observe the atomic image and is heated, cooled or kept at room temperature by using the scanning type probe microscope, namely, after the atomic image of the probe is observed by the probe, or while observing the atomic image, the atom to be removed from the probe to be machined, the atom to be added thereto, the atom to be moved and are determined, a pulse having a suitable width, a suitable voltage and a polarity is once or repeatedly applied between the two probes, and the above-mentioned determined atom is removed, added or moved so as to stably project one atom at the end of the probe to be machined to thereby form a sharp probe having one atom at the end, or the surface of the sample is analyzed by using the probe having one atom at the end.

10. A super short high voltage pulse applying method in a scanning type probe microscope, comprising the steps of:
applying a first super short AC or DC high voltage pulse to a coaxial cable from a pulse power source in order to apply the first super short high voltage pulse between a probe of the scanning type probe microscope and a sample, a terminal of the coaxial cable being connected to one of the probe and the sample, and the other side being kept substantially at ground potential, an outer conductive sheath of the coaxial cable being cut at the terminal and a core line being exposed to be as short as possible so that the terminal of the coaxial cable may be regarded as an open end, the core line being connected to one of the probe and the sample;
applying a second super short high voltage pulse having twice as much power as the first super short high voltage pulse due to a power reflection at the open end of the coaxial cable between the probe and the sample without causing any strain to its waveform; and
superposing, at the same time, a bias voltage to the first super short high voltage pulse or otherwise using the ground potential as the bias potential.

11. The super short high voltage pulse applying method in a scanning type probe microscope according to claim 10, wherein in order to repeatedly apply the super short AC high voltage pulse between the probe and the sample, a pulse microwave generated in a pulse magnetron is transferred in order of an attenuator for adjusting a power, a reflected power absorbing means for absorbing the reflected power and a adjustment means for machining an impedance, the super short AC high voltage pulse is fed to the coaxial cable through a coaxial waveguide convertor for converting the transfer line from the waveguide for constituting the attenuator, the reflected power absorbing means and the adjustment means to the coaxial cable, a chalk flange for DC insulation and a bias voltage applying circuit for applying a DC bias voltage are added to the coaxial waveguide convertor.

12. The super short high voltage pulse applying method in a scanning type probe microscope according to claim 10, wherein in order to repeatedly apply the super short DC high voltage pulse between the probe and the sample, the super short DC high voltage pulse generated by a super short DC high voltage pulse repeating generator is applied in order to an attenuator for adjusting the power, and a reflected power absorbing means for absorbing the reflected power, the super short DC high voltage pulse is fed to the coaxial cable, and the DC bias voltage is applied by a DC bias voltage superposing function provided in the super short DC high voltage pulse generator or a bias tee provided between the attenuator and the reflected power absorbing means and a bias voltage applying circuit.

13. A super short high voltage pulse applying method in a scanning type probe microscope, comprising the steps of:
applying a super short AC or DC high voltage pulse to a coaxial cable from a pulse power source in order to apply the super short high voltage pulse between a probe of the scanning type probe microscope and a sample, a terminal of the coaxial cable being connected to one of the probe and the sample, and the other side being kept substantially at ground potential, an outer conductive sheath of the coaxial cable being cut at the terminal and a core line being exposed to be short as much as possible so that the terminal of the coaxial cable may be regarded as an open end, the core line being connected to one of the probe and the sample; and
applying a super short high voltage pulse having twice as much power as the first-mentioned super short high voltage pulse due to a power reflection at the open end of the coaxial cable between the probe and the sample without causing any strain to its waveform.

14. The super short high voltage pulse applying method in a scanning type probe microscope according to claim 13 or 10, further comprising the step of utilizing a phenomenon that an electron discharged from one of the probe and the sample is repulsively dispersed at the surface of the other, wherein a maximum energy of the repulsively dispersed electron is analyzed by an electron energy analyzer, and a maximum voltage of the super short high voltage pulse applied between the probe and the sample is measured.

15. The super short high voltage pulse applying method in a scanning type probe microscope according to claim 13 or 10, further comprising the step of utilizing a phenomenon that a photon discharged from one of the probe and the sample is braked and radiated at a certain probability when the electron discharged emitted from one of the sample and the probe is collided to the surface of the other of the sample and the probe, wherein a maximum energy of the photon is analyzed by an electron energy analyzer, and a maximum voltage of the super short high voltage pulse applied between the probe and the sample is measured.

16. The super short high voltage pulse applying method in a scanning type probe microscope according to claim 13, wherein in order to repeatedly apply the super short AC high voltage pulse between the probe and the sample, a pulse microwave generated in a pulse magnetron is transferred in order of an attenuator for adjusting a power, a reflected power absorbing means for absorbing the reflected power and a adjustment means for machining an impedance, and the super short AC high voltage pulse is fed to the coaxial cable through a coaxial waveguide convertor for converting the transfer line from the waveguide for constituting the attenuator, the reflected power absorbing means and the adjustment means to the coaxial cable.

17. The super short high voltage pulse applying method in a scanning type probe microscope according to claim 16, wherein a waveguide type isolator or a circulator and a dummy load are used in combination as the reflected power absorbing means.

18. The super short high voltage pulse applying method in a scanning type probe microscope according to claim 16, wherein a waveguide type E/H tuner or a three stab tuner is used as the adjustment means.

19. The super short high voltage pulse applying method in a scanning type probe microscope according to claim 13, wherein in order to repeatedly apply the super short DC high voltage pulse between the probe and the sample, the super short DC high voltage pulse generated by a super short DC high voltage pulse repeating generator is applied in order to an attenuator for adjusting the power, and a reflected power absorbing means for absorbing the reflected power, and the super short DC high voltage pulse is fed to the coaxial cable.

20. The super short high voltage pulse applying method in a scanning type probe microscope according to claim 19, wherein a waveguide type isolator or a circulator and a dummy load are used in combination as the reflected power absorbing means.

* * * * *